Dec. 13, 1966 M. L. MEILLAND Plant Pat. 2,691
ROSE PLANT
Filed Oct. 12, 1965
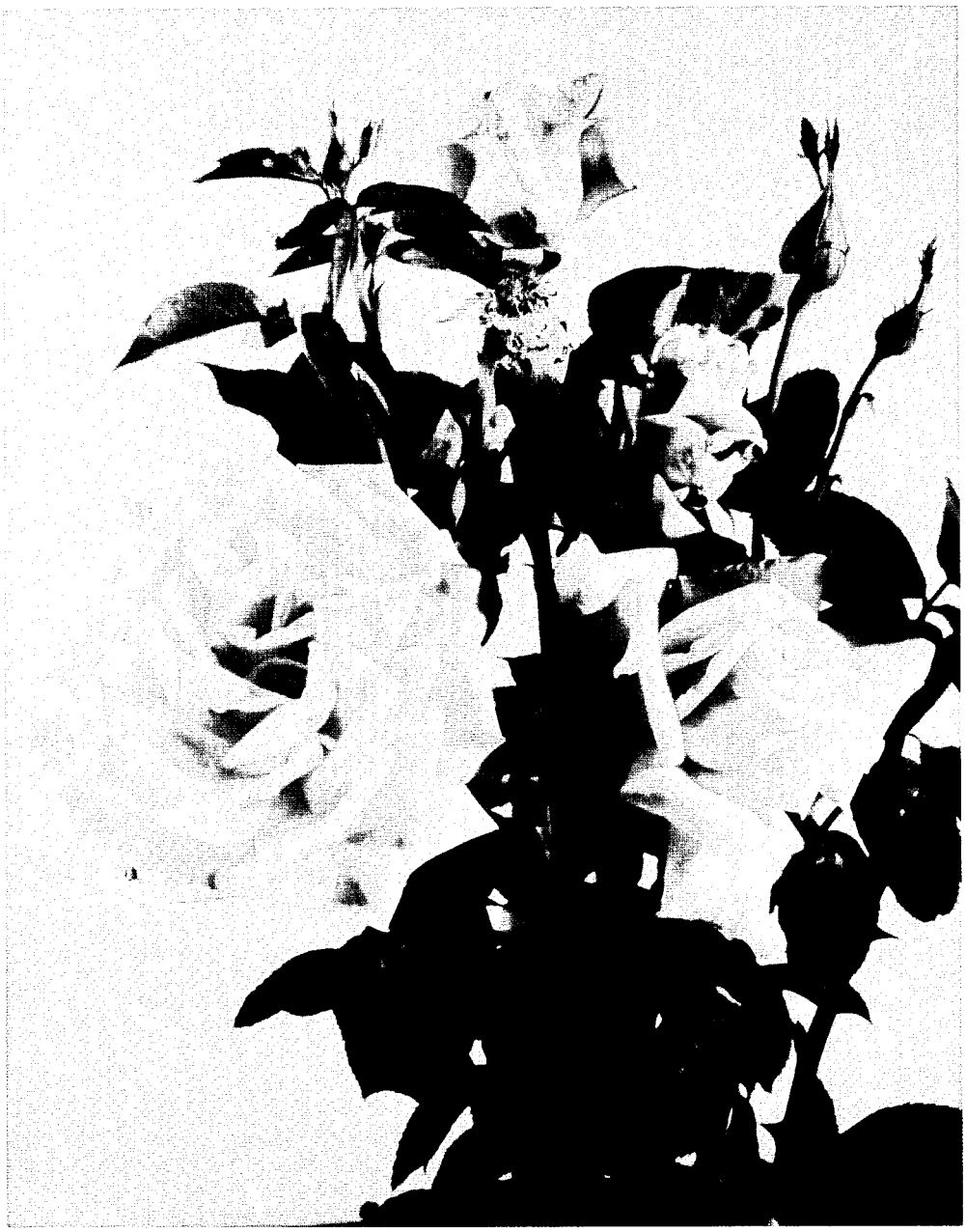
Inventor.
Marie Louise Meilland
By: Robb & Robb
Attorneys.

United States Patent Office

Plant Pat. 2,691
Patented Dec. 13, 1966

2,691
ROSE PLANT

Marie Louise Meilland, Alpes Maritimes, France, assignor to The Conard-Pyle Company, West Grove, Pa., a corporation of Pennsylvania

Filed Oct. 12, 1965, Ser. No. 495,364
1 Claim. (Cl. Plt.—18)

The present invention relates to a new and distinct variety of Rose plant of the hybrid tea class, which was originated by me by crossing an unnamed and unpatented seedling of unidentified parentage with the variety known as "Simone" (U.S. Plant Patent No. 1,847).

As the result of this breeding, I have produced a new and improved rose variety which is distinguished from its parents, as well as from all other varieties of which I am aware, as evidenced by the following unique combination of characteristics which are outstanding therein:

(1) A vigorous and upright habit of growth;

(2) A distinctive and attractive size, shape and color of the foliage;

(3) The presence of comparatively few prickles on the flowering canes;

(4) A high-centered flower form, with the flower petals loosely rolled outward, from the beginning to maturity; and (5) A distinctive and attractive Pale Purplish-Pink (Pale Lilac) general color tonality of the flowers.

In comparison with its unnamed seed parent, the flowers of my new variety possess superior petalage, with an average of 60 petals per flower, while the flowers of this parent are not as full and average only 25 petals, and the flowers are lighter in color and are pale Lilac, whereas those of this parent are light fuchsine in color.

As compared with its pollen parent, "Simone," the habit of growth of the new variety is superior and more balanced; the foliage is generally smaller; the necks of the flowers are erect and stiff and are not prone to bend under certain weather conditions like those of this parent; and while the flowers are not as large, they are of superior form.

Asexual reproduction of the new variety by budding, as performed in France, and also at West Grove, Pennsylvania, U.S.A., shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color teminology in accordance with the Horticultural Colour Chart of the Royal Horticultural Society (hereinafter abbreviated as (H)) and the Nickerson Color Fan, published by Munsell Color Company, Inc., of Baltimore, Maryland, U.S.A. (hereinafter abbreviated as (N)), as indicated, except where general color terms of ordinary dictionary significance are obvious:

Type: Hardy; bush; outdoor; seedling; for garden decoration.
Class: Hybrid tea.
Breeding: Seedling.
*Seed parent.*—An unnamed seedling of unidentified parentage.
*Pollen parent.*—"Simone."
Propagation: Holds its distinguishing characteristics through succeeding propagations by budding.

*Flower*

Locality where grown and observed: West Grove, Pennsylvania, U.S.A.
Flowers borne: Usually singly, but sometimes several to stem; on stems of medium length and normal strength.
Quantity of bloom: Abundant, outdoors.
Continuity: Continuous.
Fragrance Slight:. Nature—tea.
Bud:
*Peduncle.*—Medium length; medium caliper; erect; rough; with medium number of red glandular-tipped hairs. Color—reddish overlying green.
*Before calyx breaks.*—Size—medium. Form—medium length; pointed ovoid; with a conspicuous neck; with foliaceous appendages on the surface of the bud; with bristle-like foliaceous parts extending beyond the tip of the bud equal to ½ or more of its length.
*As calyx breaks.*—Color—Rose Opal, Plate 022/1 (H) at tip of bud, gradually changing to dull greenish-yellow at base of petal.
*As first petal opens.*—Size—medium. Form—medium length; urn-shaped. Color: outside—Pale Purplish-Pink, Plate 10P 8/5 (N) with small zone of Brilliant Yellow-Green, Plate 2.5GY 8/9 (N) surrounding the point of attachment; inside—near Pale Purplish-Pink, Plate 10P 8/5 (N), washed toward the outer margin with Moderate Purplish-Pink, Plate 2.5RP 7/8 (N), with base of petal surrounding point of attachment Brilliant Yellow-Green, Plate 2.5GY 9/8 (N).
*Opening.*—Opens up well.
Bloom:
*Size (when fully open).*—Medium; from 4 inches to 4½ inches.
*Petalage.*—Double; from 55 to 65 petals; arranged irregularly.
*Form.*—High-centered at first and remaining high-centered; petals being at first loosely rolled outward and remaining loosely rolled outward at maturity.
Petals:
*Texature.*—Medium thickness.
*Appearance.*—Inside—satiny. Outside—satiny.
*Shape.*—Outer petals—ovate. Intermediate petals—ovate. Inner petals—ovate.

This description of a newly opened flower was made from a rose grown outdoors during the month of August at West Grove, Pennsylvania, U.S.A.:

*Color.*—Outer petal: Outside surface—between Pale Purplish-Pink, Plate 2.5RP 9/2 (N) and Pale Purplish-Pink, Plate 10P 8/5 (N), except for a small area surrounding point of attachment of Brilliant Yellow-Green, Plate 2.5GY 8/9 (N), inside surface—Light Purplish-Pink, Plate 2.5RP 8/5 (N) and at the margin becoming progressively lightened to Pale Purplish-Pink, Plate 2.5RP 9/2 (N) toward the base, and thence to almost white, with small area surrounding point of attachment Brilliant Yellow-Green, Plate 2.5GY 9/8 (N). Intermediate petal: Outside surface—between very Pale Purple, Plate 7.5P 9/2 (N) and very Pale Purple, Plate 7.5P 8/5 (N), with two small areas of Light Yellowish-Pink, Plate 7.5R 9/3 (N) on either side of the point of attachment bordering a small area of Brilliant Greenish-Yellow, Plate 7.5Y 9/8 (N), inside surface—between very Pale Purple, Plate 7.5P 8/5 (N) and Pale Purplish-Pink, Plate 10P 8/5 (N), except for a small area surrounding point of attachment of Brilliant Greenish- Yellow, Plate 7.5Y 9/8 (N). Inner petal: Outside surface—Light Purplish-Pink, Plate 7.5RP 8/5 (N), with area surrounding point of attachment Brilliant Greenish-Yellow, Plate 7.5Y 9/8 (N); inside surface—between Light Purplish-Pink, Plate 5RP 8/5 (N) and Light Purplish-Pink, Plate 2.5RP 8/5 (N), with area surrounding point of attachment Brilliant Greenish-Yellow, Plate 10Y 9/9 (N).

This description was made from a rose that was open for three days outdoors during the month of August at West Grove, Pennsylvania, U.S.A.:

*Color.*—Outer petal: Outside surface—Pale Purplish-Pink, Plate 10P 8/5 (N), becoming progressively lighter toward base of petal; inside surface—Pale Purplish-Pink, Plate 10P 8/5 (N), becoming progressively lighter toward base of petal, then almost white surrounding point of attachment. Inner petal: Outside surface—between Pale Purplish-Pink, Plate 2.5RP 9/2 (N) and Pale Purplish-Pink, Plate 10P 8/5 (N), with small area of Brilliant Greenish-Yellow, Plate 7.5Y 9/8 (N); inside surface—between very Pale Purple, Plate 7.5P 8/5 (N), and Pale Purplish-Pink, Plate 2.5RP 9/2 (N), with area surrounding point of attachment near Brilliant Greenish-Yellow, Plate 7.5Y 9/8 (N).

*General color effect.*—Newly opened flower—Pale Purplish-Pink, Plate 10P 8/5 (N). Three days open—between very Pale Purple, Plate 7.5P 8/5 (N) and Pale Purplish-Pink, Plate 10P 8/5 (N).

*Behavior.*—Drop off cleanly; becomes paler in old age.

*Flower longevity.*—On bush in garden—5 days in August. Cut roses grown outdoors and kept at living room tempearture—4 days in August.

*Reproductive organs*

Stamens: From few to medium number; arranged irregularly about pistils; mixed with petaloids.

Filaments: Most with anthers; medium length or long. Color—pale yellow.

Anthers: Open at various times; from small to medium size; occasionally an anther fused with a petaloid. Color—yellow.

Pollen: Sparse. Color—gold.

Pistils: From medium number to many.

Styles: Uneven; medium length; medium caliper; bunched.

Stigma: Color—yellow.

Ovaries: Some protruding from receptacle.

Hips: Medium length; globular; with inconspicous neck; very smooth; walls medium thick and fleshy. Color—green.

Sepals: Permanent; moderately long; spear-shaped.

Seeds: Medium number; medium size.

*Plant*

Foliage:

*Leaves.*—Compound of 3 or generally 5 leaflets; normal abundance; large size; leathery.

*Leaflets.*—Shape—oval. Apex—acute. Base—obtuse. Margin—simply serrate.

*Color.*—Mature: Upper surface—Spinach Green, Plate 0960 (H); under surface—Sage Green, Plate 00086 1/1 (H). Young: Upper surface—Spinach Green, Plate 0960 (H), heavily overlaid with Beetroot Purple, Plate 830/2 (H); under surface—near Beetroot Purple, Plate 830/2 (H).

*Rachi (the supporting stem of the compound leaf).*—Medium caliper. Upper side—grooved; hairy. Under side—sparsely prickly.

*Stipules.*—Moderately long; medium width; with short points turning out at an angle of more than 45°.

*Disease resistance.*—Comparable to that of the average variety grown under the same cultural conditions at West Grove, Pennsylvania, U.S.A.

Growth:

*Habit.*—Bushy; upright; much-branched.

*Growth.*—Free.

*Canes.*—Medium caliper.

*Main stems.*—Bright. Color—Fern Green, Plate 0862 (H). Prickles—several; color—brown. Hairs—none.

*Branches.*—bright. Color—Fern Green, Plate 0862 (H). Prickles—few; color—brownish. Hairs—none.

*New Shoots.*—Color—Fern Green, Plate 0862 (H), overlaid with Erythrite Red, Plate 0027 (H). Prickles—few; color—reddish. Hairs—none.

I claim:

A new and distinct variety of rose plant of the hybrid tea class, substantially as herein shown and described, characterized particularly as to novelty by the unique combination of a vigorous and upright habit of growth, a distinctive and attractive size, shape and color of the foliage as described and shown, the presence of comparatively few prickles on the flowering canes, a high-centered flower form, with the flower petals loosely rolled outward, from the beginning to maturity, and a distinctive and attractive Pale Purplish-Pink (Pale Lilac) general color tonality of the flowers.

No references cited.

ABRAHAM G. STONE, *Primary Examiner*,

R. E. BAGWILL, *Assistant Examiner*.